US008124010B2

(12) United States Patent
Gabel et al.

(10) Patent No.: US 8,124,010 B2
(45) Date of Patent: Feb. 28, 2012

(54) TRANSFER CONTAINER FOR PHARMACEUTICAL RECIPIENTS

(75) Inventors: Rolf-Dieter Gabel, Schwetzingen (DE); Martin Knierim, Mannheim (DE)

(73) Assignee: F. Hoffman-La Roche AG, Basel (CH)

( * ) Notice: Subject to any disclaimer, the term of this patent is extended or adjusted under 35 U.S.C. 154(b) by 70 days.

(21) Appl. No.: 12/855,491

(22) Filed: Aug. 12, 2010

(65) Prior Publication Data

US 2011/0024419 A1    Feb. 3, 2011

Related U.S. Application Data

(63) Continuation of application No. PCT/EP2008/065690, filed on Nov. 17, 2008.

(30) Foreign Application Priority Data

Feb. 14, 2008 (EP) .................................... 08151420

(51) Int. Cl.
| | |
|---|---|
| A61L 2/08 | (2006.01) |
| A61L 2/00 | (2006.01) |
| A61L 3/00 | (2006.01) |
| B08B 3/00 | (2006.01) |
| A47G 19/00 | (2006.01) |
| B67D 5/64 | (2006.01) |
| B60B 29/00 | (2006.01) |
| F16L 35/00 | (2006.01) |
| A61G 11/00 | (2006.01) |
| A61B 17/43 | (2006.01) |
| E06B 3/32 | (2006.01) |

(52) U.S. Cl. .................. 422/1; 422/26; 422/28; 422/40; 422/63; 422/545; 422/559; 422/292; 422/297; 422/300; 134/61; 134/85; 134/92; 137/343; 137/583; 220/23.4; 220/23.88; 220/500; 220/538; 220/539; 220/540; 220/315; 220/DIG. 20; 222/153.01; 222/160; 414/429; 285/80; 285/284.1; 312/1; 312/246; 312/249.1; 312/249.8; 312/291; 604/905; 49/380; 49/463

(58) Field of Classification Search ................. 422/1, 26, 422/28, 40, 63, 545, 559, 292, 297, 300; 134/61, 85, 92; 137/343, 583; 220/23.4, 220/23.88, 500, 538–540, 315, DIG. 20; 222/153.01, 160; 414/429; 285/80, 284.1; 312/1, 246, 249.1, 249.8, 291, 293.3; 604/905; 49/380, 463

See application file for complete search history.

(56) References Cited

U.S. PATENT DOCUMENTS

| 5,792,422 A | 8/1998 | Lin et al. |
| 2003/0235511 A1 | 12/2003 | Jacobs et al. |

FOREIGN PATENT DOCUMENTS

| DE | 10 17 454 | * 10/1957 |

(Continued)

OTHER PUBLICATIONS

European Patent English Translation of DE 10 17 454.*

(Continued)

*Primary Examiner* — Jill Warden
*Assistant Examiner* — Monzer Chorbaji
(74) *Attorney, Agent, or Firm* — Bose McKinney & Evans LLP (57) ABSTRACT

A reusable container for the sterile transfer of pharmaceutical recipients, in particular of syringe bodies. The container comprises an outer case and a sterilizable interior, wherein the interior is microbially isolated from the environment of the container. The interior has at least one holder for accommodating at least one nest for storing a plurality of pharmaceutical recipients. The nest can be removably accommodated in the holder. The container further has at least one container door for removing or introducing the nest into the interior and at least one lock for coupling the container to a sterile space. The lock is configured in such a way that, after coupling to the sterile space, it is possible to open the container door without substantially suspending sterility.

33 Claims, 3 Drawing Sheets

FOREIGN PATENT DOCUMENTS

| | | |
|---|---|---|
| DE | 19756808 | 6/1998 |
| DE | 44 19 475 | 6/2007 |
| DE | 102006036460 | 7/2008 |
| WO | WO 9606780 | 7/1996 |

OTHER PUBLICATIONS

PCT Interntional Preliminary Report on Patentability, Oct. 14, 2010, PCT Application No. PCT/EP2008/065690 (English Translation).

* cited by examiner

TRANSFER CONTAINER FOR PHARMACEUTICAL RECIPIENTS

RELATED APPLICATIONS

This application is a continuation of PCT/EP2008/065690, filed Nov. 17, 2008, which claims priority to EP08151420.0, filed Feb. 14, 2008, both of which are hereby incorporated by reference in their entirety.

BACKGROUND

The invention relates to a reusable container for the transfer of sterile pharmaceutical recipients. The invention further relates to a transfer system for the sterile transfer of pharmaceutical recipients and also to a method for filling pharmaceutical recipients with at least one pharmaceutical medium. Containers, transfer systems and methods of this type may be used in particular in the field of the manufacture and/or bottling of pharmaceutical recipients, such as, for example, medicaments, diagnostic agents or the like. However, as a matter of principle, the invention can also be used in other sectors requiring a transfer of any type of low-germ or sterile recipients, for example in the fine chemicals sector or in the food industry sector.

The transfer of recipients under sterile conditions is important in many areas of natural science and technology. Examples of this include, as stated above, pharmaceutical production or bottling in which medicinal products (for example, pharmaceutical agents, pharmaceutical composition preparations, diagnostic agents, diagnostic agent-containing preparations and/or therapeutic media) are poured into suitable recipients. A further possible area of application is the treatment or handling of biological samples. Further areas are the foodstuff industry which also requires at least a low germ count. Pharmaceutical production will be described hereinafter without restricting possible further applications of the invention.

In the pharmaceutical industry, a large number of bottling technologies are used for manufacturing in particular filled single-use syringes, known as ready-to-use syringes, under aseptic, i.e., at least largely germ-free, conditions. As a matter of principle, a distinction is drawn in this case between what are known as line filler technologies and what are known as tray filler technologies, although further bottling techniques can also be used. The present invention relates in particular to tray filler technologies, but can also be used for other bottling technologies, for example line filler technology.

In tray filler technology, unfilled, initially non-sterile syringe bodies (what are known as ready-to-fill syringe bodies) are introduced at a packaging supplier's factory into what are known as trays which are conventionally made of plastics material. The trays are in this case conventionally embodied as upwardly open shells having a raised edge. These trays are equipped with internal plastics material racks (also referred to as a nest) into which the previously cleaned and closed-tipped syringe bodies are inserted with the tip hanging downward. The trays with the racks and the syringe bodies are then generally covered or closed with a plurality of layers of foils which are loose or welded to the tray (a type of shell) and subsequently sterilized generally with ethylene oxide or if appropriate other methods. The multiple covering or closing prevents microbial contamination after the sterilization. The sterile syringe bodies packaged in this way in the trays are then delivered to the pharmaceutical agent manufacturer and/or the bottling factories. There, the trays are opened for filling the syringe bodies under aseptic clean room and handling conditions and the syringe bodies are generally brought together with the tray and rack to a special bottling machine (tray filler machines). There, the syringes are then filled and closed after filling—generally while still in the tray or rack or nest. The filled, closed syringes are subsequently, during what is known as "de-nesting", removed from the trays, generally by machine, and further processed. The trays and racks are left behind, as are the protective foils, all of which are generally not reused and constitute considerable waste.

An example of a document describing conventional bottling technologies of this type is DE 44 19 475 A1. Said document describes methods which relate in particular to tray filler technology and reference may be made to said document for further details of possible bottling processes and tray filler technology. DE 44 19 475 A1 discloses a means for removing the covering of storage boxes, such as can, for example, be used as trays in tray filler technology.

However, DE 44 19 475 A1 already makes some of the drawbacks of known technologies apparent. Thus, the large-scale handling of the previously used, welded trays equipped with a plurality of protective foils is extremely costly. Special devices, such as, for example, the device described in DE 44 19 475 A1, have to be used in order to open the outer packagings of the sterilized syringe bodies and in order to remove the nests from the trays.

Furthermore, the trays equipped with as-yet-unfilled syringe bodies (or if appropriate other primary packagings) take up a lot of storage space. Furthermore, special bottling machines (tray fillers) are required that are specially designed for filling the syringe bodies which reach the bottling station in the trays.

A further drawback of the above-described method, which is becoming increasingly important, is the large amount of waste incurred in this method. Thus, the single-use outer packagings, which are disposed of after the removal of the syringe bodies or the trays, are valuable raw materials which are generally wasted without being re-used. This not only constitutes a considerable cost factor, but can also cause considerable environmental problems in large-scale bottling operations.

US 2003/0235511 A1 describes a method for sterilization by means of chemical vapors. This method uses a sterilization chamber which is connected to a vacuum pump and a vaporizer. The articles to be sterilized are inserted in trays or containers. The trays or containers are then encased with a material which is permeable to the sterilizing vapors. This method thus also has the above-described drawbacks that the method is associated with a large amount of waste and for large-scale use would require costly devices which remove the casings.

A further important point in a large-scale implementation of bottling technologies is the reversibility of the methods. If for example the bottling, be it in a line filler or in a tray filler installation, has to be briefly interrupted, for example on account of technical malfunctions, then it should be readily possible to return the recipients to be filled to the transfer container used and to temporarily store them there without the recipients thereby becoming contaminated and without costly devices being required for this purpose. The above-described methods of DE 44 19 475 A1 or US 2003/0235511 A1 do not satisfy these requirements, as in this method a costly renewed casing would be required during a return to the containers.

DE 1 017 454 A proposes a method for the sterile packaging of liquids, in particular milk, in which presterilized packaging material is supplied in closed containers in the form of cartridges to a sterile cabin. In this case, a closed removal end of the cartridge is coupled to a likewise initially closed entrance opening to the sterile cabin for the packaging material via a separately sterilizable coupling space which is closed on all sides. By way of example, said document states how the packaging material in the form of cups, which can be placed one inside another, is accommodated in the cartridge. However, this method is not suitable either for ensuring the above-described temporary storage in the event of an interruption to the bottling process, as the described process of accommodating in cartridges in many cases does not allow the removal to be reversed. In addition, although the described cartridges are suitable for milk recipients, they can lead in the case of sensitive glass recipients, which usually cannot be placed one inside another, to damage and even soiling caused by splinters of glass.

SUMMARY OF THE INVENTION

These teachings provide a device and a method which avoids the drawbacks of the devices and methods known in the art. In particular, the disclosed embodiments are intended to allow a sterile transfer of pharmaceutical recipients from a first sterile space to a second sterile space without the sterile atmosphere being substantially suspended during this transfer, wherein at the same time the waste produced during the transfer is to be at least largely reduced. It should in this case as a matter of principle be possible to configure the transfer so as to be reversible even in the sterile state.

A basic idea of these teachings resides in the possibility of resolving the dilemma, on the one hand, of wishing to dispense with costly sterilization of the pharmaceutical recipients in bottling lines and, on the other hand, of having to ensure sterility at the bottling site by using a suitable reusable container. The reusability of the container, which can take place for example as a result of the selection of suitable, multiple sterilizable materials which are able to withstand the mechanical loads during transfer, also prevents waste caused by single-use packagings.

A reusable container for the sterile transfer of pharmaceutical recipients, in particular of syringe bodies, is therefore proposed. The pharmaceutical recipients can for example contain syringe bodies, ampules, phials, bottles, glasses or similar recipients which are suitable for accommodating solid and/or gaseous and/or liquid ingredients. As stated above, the term "pharmaceutical" includes in this connection both diagnostic media and media with active substances for causing at least one medicinal effect. However, the container disclosed herein is as a matter of principle not restricted to pharmaceutical recipients.

The container comprises at least one outer case with a sterilizable interior. The term "sterilizable" refers in this case to the fact that the container displays at least extensive resistance to at least one common sterilizing method. In particular, this may be resistance to thermal sterilization (for example up to a predefined minimum temperature, for example a temperature above 80° C.) by means of hot air and/or superheated steam. For example, typical hot air sterilization can include exposure to temperatures in the range of from 180° C. to 340° C. Alternatively or additionally, this may also be at least extensive resistance to sterilization by ray sources (for example electromagnetic ray sources, in particular UV light, and/or radioactive ray sources, such as for example gamma ray sources) or resistance to suitable chemicals for the sterilization, for example by means of gases or other fluid media, for example ethylene oxide, hydrogen peroxide, formaldehyde or the like. Preferably, this at least partial resistance is configured in such a way that a large number of sterilization cycles of this type are possible without the container (i.e., the outer case and/or components accommodated inside the container, for example an inner container) experiencing a change (for example surface, shape or material changes).

The interior is microbially isolated from the environment of the container. In order to bring about this isolation, the container can for example have suitable sealing elements, for example rubber seals or the like, which in principle prevent microbial impurities from infiltrating the container. The term "in principle" refers in this connection to an optimization, corresponding to the conventional standard, of the prevention of the infiltration of microbial impurities in which no microbial impurities infiltrate the interior over a period of time which is required in practice and under conventional conditions which are required for transferring and storing the pharmaceutical recipients (for example a few hours up to a few months, under fluctuating environmental conditions (e.g. temperature, air pressure) and also under mechanical loads).

The interior has at least one holder for accommodating at least one nest for storing a plurality of pharmaceutical recipients. As described above, this nest can for example comprise a planar plate which may also be referred to as the "nest body". The nest body, which can be configured in a substantially planar manner, can then have a plurality of openings for introducing, for example suspending, the pharmaceutical recipients. These openings can for example be arranged in a regular matrix, in a linear arrangement or in a hexagonal, especially compact arrangement. The nests can for example be made of one or more materials which are resistant to sterilization, for example sterilization of the above-described type, for example appropriate plastics materials (for example fluorinated plastics materials, in particular polytetrafluoroethylene or PTFE) and/or of metals, ceramics, composite materials or the like. It is particularly preferable if the container is configured in such a way that the container can accommodate a large number of nests of this type, so that sterilized pharmaceutical recipients can be transferred in a particularly efficient manner, preferably in quantities of from several 100 to several 1,000. The at least one holder can accordingly comprise a holder which is adapted to the at least one nest, for example rails, hinges, depressions or the like; this ensures a safe (for example substantially vibration-free and slip-proof) and preferably reversible transferring of the nests or pharmaceutical recipients. In particular, the holders are to be configured in such a way that the nests are mounted so as to be removable (for example retractable and/or extendable) therefrom.

The transfer of the nests under sterile conditions requires as a matter of principle no casing, in particular no microbially tight casing, of the nests. Accordingly, the method using the container is carried out preferably without using a casing. Such a casing is undesirable in the sense of the above-mentioned reduction of waste and further industrial processability which is as straightforward as possible.

The container further has at least one container door for removing and/or introducing the nest into the interior. This container door can as a matter of principle be configured in a large number of known ways, for example as a folding door, sliding door or the like. In this case, the door is configured in such a way, for example by means of suitable sealing elements, that the interior is still microbially isolated from the environment of the container when the door is closed. It is particularly preferable if this container door is arranged on the upper side and/or, preferably, on a side wall of the container (for example an end face of a cuboid container). This container door can in particular comprise a pivoting door, in particular an outwardly opening pivoting door, in particular a bulkhead.

Additionally, the container comprises at least one lock for coupling the container to a sterile space. The term "a lock" refers in this case to any desired coupling mechanism allowing mechanically stable connection of the container to a sterile space. Examples of this include bayonet closures, although other types of locks are also possible, for example locks with corresponding lock hooks, slides, flaps or the like. The person skilled in the art is as a matter of principle familiar with locks of this type from other technical sectors. However, according to these teachings, the lock of the container is configured in such a way that, after coupling to the sterile space, it is possible to open the container door at least without substantially suspending sterility. This opening of the container door can in particular take place from the sterile space. The term "at least without substantially suspending sterility" refers in this case in particular to the fact that the lock, when coupled, is microbially shielded by the container door from an outer region surrounding the container (which is located outside the sterile space). For this purpose, the lock can for example again comprise at least one appropriate seal, for example a seal using a metal ring or metal frame, a plastics material ring or plastics material frame or a seal using a rubber ring or rubber frame. Other types of seals are in this case also possible in principle. It goes without saying that the term "at least without substantially suspending sterility" does not in this case rule out the possibility that microorganisms present in the (preferably low) volume which is formed after the coupling of the container to the sterile space between the container door and the sterile space may be contained. This volume can if appropriate be additionally sterilized before the container door is opened and/or be emptied, for example by evacuation by means of a suitable evacuation device. This could optionally ensure sterility during the transfer between the container and the sterile space.

The described container can thus be used in such a way that the transfer of pharmaceutical recipients to the sterile space preferably dispenses with trays and multiple protective foils. The pharmaceutical recipients can thus for example be cleaned at the supplier's factory and for example be pretreated as required (for example closed at the syringe tip by a cap). The pharmaceutical recipients can also additionally be closed, after introduction into the nests or beforehand, with thin protective foils at their ends, thus allowing additional protection from the infiltration of all types of floating particles to be ensured.

The pharmaceutical recipients, in particular the syringe bodies, can be cleaned and/or sterilized prior to introduction into the container or be sterilized after introduction in the interior of the container. The interior per se can also be cleaned and/or sterilized before the contents are introduced into the container.

The interior of the container comprises, depending on its size and the pharmaceutical recipients, preferably a few hundred or more pharmaceutical recipients and thus generally replaces a large number of trays. The closed container, which is internally sterilized along with its contents, can for example be brought from the manufacturer of the recipients up to the pharmaceutical agent manufacturer or to the bottling factory for filling with the pharmaceutical medium. On the pharmaceutical agent manufacturer's premises or at the bottling factory, the container is for example brought to a sterile space and coupled there to a lock (referred to hereinafter as the "sterile lock") of the sterile space. Afterwards, the container is opened, for example automatically, semiautomatically or by hand, and its interior is exposed along with the contents toward the sterile space in such a way that the sterility of the inside of the container along with its contents remains at least largely ensured.

The contents of the container, i.e., the nests and the pharmaceutical recipients, can be removed in different ways, for example by removing the pharmaceutical recipients from the nests, the nests remaining wholly or partly in the interior of the container. Alternatively, the nests can also be removed together with the pharmaceutical recipients from the container or an inner container thereof. Furthermore, the nests can also be extended together with the pharmaceutical recipients from the container or an inner container, without being completely removed. In a further alternative, the container contains an inner container inside which the holders are accommodated for accommodating the at least one nest. In particular in this alternative, but also in other embodiments, it is particularly advantageous if the nests do not contain an individual, for example microbially tight, casing. The container door should then be configured in such a way that the inner container is reversibly removable from the interior of the container. In this case, the inner container can be removed from the container along with the nests and the pharmaceutical recipients contained therein and brought for example to the sterile space.

If the nests are removed from the container or the inner container thereof along with the empty pharmaceutical recipients, then the nests can be brought up to or onto a bottling line. For this purpose, it is particularly advantageous if the nests do not contain any individual microbially tight casing. Suitable molded parts can allow the nests to be processed on what is known as a conventional line filler bottling machine. Line filler bottling machines are a common pharmaceutical manufacturing technology. An operator's own tray filler bottling machine is thus generally not required, but can also be used as a matter of principle.

The pharmaceutical recipients can be filled, if appropriate after removal of an additional seal (such as for example the above-mentioned thin protective foil for preventing the infiltration of particles or other impurities), filled and then closed by means of a common technology, for example with plugs or other closures. The closed pharmaceutical recipients filled in this way are then for example removed from the nests by means of a common "de-nesting technique".

As an alternative to supplying nests up to or onto the bottling line, the empty pharmaceutical recipients can be removed from the nests before entering the bottling line and placed onto the bottling line individually or in groups. This alternative is advantageous in particular when the pharmaceutical recipients in the nests are arranged in a geometry which does not allow the nests to be processed along with the syringe bodies on a conventional bottling line without additional complex machinery. For these method alternatives too, it is advantageous if the nests do not contain an individual, in particular microbially tight, casing.

Empty nests can then be returned to a container or an inner container, the inner container then for example being introduced into a container again. For this purpose, use may be made of either the same container and/or inner container from which the nests were previously removed or else a second container with an inner container. The requirements in terms of sterility are no longer as stringent in this regard as in the delivery of the unfilled pharmaceutical recipients. The container equipped with empty nests, with or without an inner container, is then locked out of the sterile space or undocked from the lock thereof in a suitable manner, preferably while maintaining aseptic clean room conditions. The container can then be transported back to the manufacturer of the pharmaceutical recipients and re-equipped there (if appropriate after cleaning) with empty pharmaceutical recipients.

In particular in the event of interruptions to the bottling process, the nests can preferably be temporarily returned from the sterile space to the container and/or the inner container while maintaining sterility. The nests can in this case contain as-yet-unfilled recipients, for example syringe bodies, but can also contain syringe bodies which have already been at least partly filled. The container equipped in this way can preferably be temporarily closed and even undocked from the sterile space. Later, the container can preferably if appropriate be redocked, if it was undocked, to the lock and can be opened in order to remove the nests for continuing the bottling process or to remove from the nests both the recipients which are still empty and the recipients, in particular syringe bodies, which have already been filled. This reversibility of the removal of nests from the container and/or inner container and also the alternative removal of syringe bodies from the nests requires, above all in an automatic or semiautomatic removal technique, a suitable arrangement of the openings for accommodating the syringe bodies in the nests. Full reversibility generally presupposes that neither the nests nor the individual syringe bodies have an individual casing. Accordingly, it is preferable if the nests are introduced into the container, in particular into the inner container, without an additional casing, in particular without an individual, closed casing. In the proposed technology, the direct waste formed is preferably merely if appropriate the thin protective foils for temporarily protecting the open empty pharmaceutical recipients.

The above-described container can be advantageously configured in various ways, wherein the advantageous developments described hereinafter can be implemented individually or in combination.

A first preferred configuration relates to the lock itself. Thus, the lock can for example comprise at least a first lock part which is connected to the outer case outside the container door and at least partly surrounds the container door. The coupling to the sterile lock of the sterile space, in particular a first sterile lock part surrounding a sterile space door, can be coupled by means of this first lock part. Furthermore, the container can comprise at least a second lock part which is connected to the container door. This second lock part can be coupled to a second sterile lock part connected to the sterile space door. Double couplings of this type are for example known from the nuclear engineering sector in which they are referred to for example as "La Calhène" locks. La Calhène locks of this type allow coupling to take place particularly efficiently and without suspending sterility, as the first lock parts and the second lock parts are for example each at the same time connected to their mating parts. The sterile space door and the container door can be opened at the same time as a result of the coupling of the second lock parts which are each connected thereto. This coupling technique is particularly advantageous for the above-described possible reversion of the unloading of the container and/or inner containers, for example in the case of the interruption of a pharmaceutical bottling process.

Further advantageous configurations of the container emerge with regard to the interior thereof. Thus, the at least one interior can for example, as described above, comprise an inner container which can be accommodated in the interior. This inner container is preferably configured as a removable inner container, for which purpose devices for reversibly accommodating the inner container can for example be provided. Like the outer container, the inner container may for example also be of rectangular, polygonal, round or similar geometrical shape or be configured with corresponding roundings. With regard to the materials which can be used, reference may be made to the above-described materials, so that for example metals (for example high-grade steel), ceramic, glass, plastics materials (in particular fluorinated plastics materials, such as for example polytetrafluoroethylene) and/or composites of materials of this type can be used both for the outer container and for the inner container. In particular, the materials, like the materials of the outer container, can be selected in such a way that the materials are able to withstand the mechanical loads occurring during use, transportation and storage and also multiple cleaning and/or sterilization cycles. In particular, the materials and the design of the container or the inner container can be configured in such a way that they ensure the microbial purity of the inside of the container. For this purpose, the materials can for example also contain additives which cause microbial disinfection, such as is known for example from refrigerators. Thus, use may for example be made of antibacterial substances which can for example be attached in and/or on plastics material or metal surfaces.

In order to ensure improved sterilization, in particular by fluid media (such as for example the above-described gases, vapors or liquids), the inner container can be configured as an open inner container, in particular as an inner container through which fluid sterilizing media can flow. For this purpose, although the inner container may for example display appropriate mechanical stability, it can for example have corresponding openings allowing sterilizing media to enter and/or flow through or act on the interior.

The pharmaceutical recipients can for example be sterilized at the factory of the manufacturer of the recipients, for example in a second sterile space. However, alternatively or additionally, the sterilization can also be carried out directly within the container, for example by means of the above-described sterilizing media. For this purpose, in particular the container, for example the outer container, can have at least one connecting opening for introducing and/or discharging at least one fluid disinfecting or sterilizing medium into or from the interior. The connecting opening can in particular be configured so as to be closable, for example by an appropriate valve, and can in particular comprise at least one port (for example a port with a standardized flange). In this way, appropriate sterilizing media (for example gases or superheated steam) for cleaning and/or sterilizing the container interiors can be introduced and discharged therefrom again.

In order to allow improved blending of the atmosphere in the container interior, for example during sterilization and/or later during transportation, one or more ventilation devices can additionally be provided inside the container.

Furthermore, the container can have, likewise in order to effect sterilization or disinfection, at least one opening, preferably an opening which can again be closed (for example again by means of a suitable valve), for introducing a radiation source into the interior. As described above, this radiation source can for example comprise an intensive light source (for example an ultraviolet light source), a differently configured, electromagnetic ray source, a radioactive ray source (for example an alpha, beta or gamma source or a combination of ray sources of this type). The container can be configured in such a way that this ray source can be introduced only temporarily via the opening in this container or the container can completely and integrally comprise a ray source of this type for disinfecting and/or sterilizing the interior or the pharmaceutical recipients. Alternatively or additionally to the aforementioned possibilities, it is furthermore possible to configure the container with at least one temperature control device for heating and/or cooling the interior. Appropriate radiant heaters and/or differently configured heating means can for example be provided for this purpose, wherein the heating can for example be carried out up to thermal disinfection.

Furthermore, the container or the interior thereof can be completely isolated from the outer region, for example by pressure-tight and/or vacuum-tight partitioning. However, as stated above, substantially all that is required is to ensure microbial shielding. For this purpose, the container can for example further comprise at least one microbial filter for filtering atmosphere circulated in the interior and/or for filtering fluid media, in particular air, infiltrating the interior.

The described container in one of the described configurations is in particular to be suitable for transportation, for example from a manufacturer of the pharmaceutical recipients to a medicament manufacturer and/or bottling factory. For this purpose, the container can for example comprise a plurality of "rolls" or "rollers", in particular rolls with braking means. The terms "rolls" or "rollers" refer in this case as a matter of principle to any desired types of devices for facilitating onward movement, i.e., in addition to rolls as such, also wheels, gear wheels, runners, rails or the like. In addition thereto, i.e. in particular in addition to a plurality of rolls, the container can optionally also comprise a plurality of bearing feet for stationarily mounting the container, for example in the form of non-rolling feet for stationarily mounting the container. This allows the load on the container rolls to be relieved during the storage of heavy containers and for example accidental rolling-away to be prevented. The bearing feet can for example be configured as extendable bearing feet which are brought into contact with the ground during stationary storage.

It is particularly preferable if a large number of the described containers can be transported individually or jointly. For this purpose, the proposed container can for example have outer shaped profiles which are configured in such a way that a plurality of containers can be stacked. For example, the containers can accordingly have corresponding depressions into which the bearing feet and/or rolls of adjacent, in particular upwardly adjoining containers can accommodate. In this way, it is possible to ensure safe stacking or safe storage, transportation, onward movement and operation of individual or joined containers. Alternatively or additionally, the container can further have at least one externally accessible coupling for coupling a transport means, for example a hook or crane hook or transport hook. Couplings of this type can for example comprise lugs or more complex couplings.

As described above, the container can have an inner container. One or more horizontally or vertically arranged rails or comparable suitable devices for reversibly accommodating nests can be provided in the interior of the container or if appropriate the inner container. The pharmaceutical recipients, which can serve as primary packaging bodies, can then be accommodated in the nests. The interior of the container can further have, as described above, devices for reversibly accommodating the removable inner container. In principle, the inner container can be made of the same materials as for example the outer case of the container, although a use of different materials, corresponding to different requirements, is also possible. The described configurations with the connecting opening, the ventilation device, the opening for introducing the radiation source, the radiation source itself, the temperature control device, the filter, and the further configurations described with reference to the container as a whole can in particular also be specially applied to the inner container. The inner container can in particular have rails or other suitable devices for accommodating the nests. The inner container, the outer container and the nests should in particular be designed in such a way that they ensure a plurality to a large number of cycles of cleaning, loading with pharmaceutical recipients, sterilization, transportation to the pharmaceutical agent manufacturer or bottler, unloading and return. In this way, the described technology allows different bottling systems (for example line fillers, tray fillers) to be supplied with ready-to-bottle primary recipients, allowing high flexibility of the described containers.

In addition to the containers in one or more of the described configurations, a transfer system is further proposed for the sterile transfer of pharmaceutical recipients to a sterile space. The transfer system comprises at least one container according to one or more of the above-described configurations, and also furthermore at least one sterile space. The term "a sterile space" refers in this case to an at least partly closed-off or shielded space in which increased freedom from germs prevails in relation to an exterior. This can for example be effected by appropriate locks, microbial filters, sterilizing means or the like. The sterile space can in particular be configured as an accessible sterile space. The sterile space has at least one sterile space wall with a sterile lock which can be coupled to the lock of the container. The sterile space can for example have at least one bottling line for bottling at least one pharmaceutical medium into the pharmaceutical recipients.

In addition to the container and the transfer system in one of the described configurations, the invention further proposes a method for filling pharmaceutical recipients with at least one pharmaceutical medium. The method can in particular be used for filling syringe bodies, although other filling media and/or other types of recipients can also be filled. In particular, the method can be carried out using at least one container according to one or more of the above-described exemplary embodiments, so that reference may largely be made to the foregoing definitions and descriptions. The method according to the invention includes the method steps described hereinafter. The steps can preferably be carried out in the indicated order, although this is not compulsory. Furthermore, one or more of the described method steps can also be carried out repeatedly, as well as simultaneously and/or with a time overlap. In addition to the described method steps, the method can also have further, non-mentioned steps.

In a first method step, a plurality of pharmaceutical recipients are manufactured and provided for use in the method. For example, these recipients can comprise glass recipients, such as for example syringe bodies. In addition to glass, other materials can also be used, for example ceramic, plastics materials, paper or composite materials.

In a further method step, the pharmaceutical recipients are sterilized. This sterilization can for example take place by means of sterilizing media (for example fluid sterilizing media, for example sterilizing liquids and/or gases and/or superheated steam) of the above-described type. Alternatively or additionally, thermal sterilizing methods, sterilization by radioactive radiation or sterilization by other types of radiation, in particular electromagnetic radiation, for example UV radiation, can also be carried out, as can steam sterilizations in general. As stated above, this sterilization can take place directly at the factory of the manufacturer of the pharmaceutical recipients and/or after the pharmaceutical recipients have been introduced into a nest and/or a container.

In a further method step, the sterilized pharmaceutical recipients that are provided in this method and are introduced into at least one nest for storing a plurality of pharmaceutical recipients. This nest is introduced into a reusable container comprising an outer case with a sterilizable interior and a container door. The interior is microbially isolated from the environment of the container and has at least one holder for accommodating the at least one nest, preferably for accommodating a large number of nests. As described above, the sterilization can also take place after the accommodation of the nests with the pharmaceutical recipients in the interior.

Subsequently, in a further method step, the container filled in this way is brought to a sterile space and coupled to the sterile space via at least one lock. With regard to the configuration of the sterile space, reference may for example be made to the foregoing discussion. In this case, the lock is configured in such a way that, after coupling to the sterile space, it is possible to open the door of the sterile space at least without substantially suspending sterility.

After this coupling, the nest is transferred to the sterile space through the container door. There, the at least one pharmaceutical medium can then be introduced into the recipients. In this case, use may for example be made of a line filler installation in which the pharmaceutical recipients are successively filled. Alternatively or additionally, use may also be made of what is known as a tray filler installation in which all of the pharmaceutical recipients located in the nest or a plurality of these recipients are filled simultaneously or the recipients are filled individually.

After the filling, the container, which is either empty or at least loaded with empty nests, can, as described above, be uncoupled from the sterile space again and be returned, for example to the site of manufacture of the pharmaceutical recipients and/or to a supplier, for example a tray supplier.

As stated above, the method can also be configured for the case of an interruption to the bottling process. Thus, it is particularly advantageous if the method can optionally be configured in such a way that at least one nest and/or at least one inner container, the latter with or without nest, can be returned to the container. The at least one nest can in this case be empty or equipped at least partly with pharmaceutical recipients. In this case, the recipients may be as yet unfilled or else at least partly already filled. A return of filled and unfilled recipients, for example a simultaneous return, is also possible. The container can then be closed, selectively while maintaining the sterile and/or aseptic state of its interior and the recipients located therein, and optionally be uncoupled, in particular undocked, from the sterile space. As stated above, this return of the pharmaceutical recipients to the container can in particular take place during an interruption to a bottling process. However, a return of this type may also be advantageous in other situations. After the ending of the interruption to the bottling process or the other event triggering the return, the container can then optionally be recoupled, in particular redocked, to the sterile space and the container can be reopened toward the sterile space, so that the pharmaceutical recipients can be transferred back to the sterile space and optionally resupplied there to a bottling process. In this method variant too, in which at least some of the pharmaceutical recipients are optionally returned to the container, it is particularly preferable if the at least one nest does not have any individual, closed casing.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
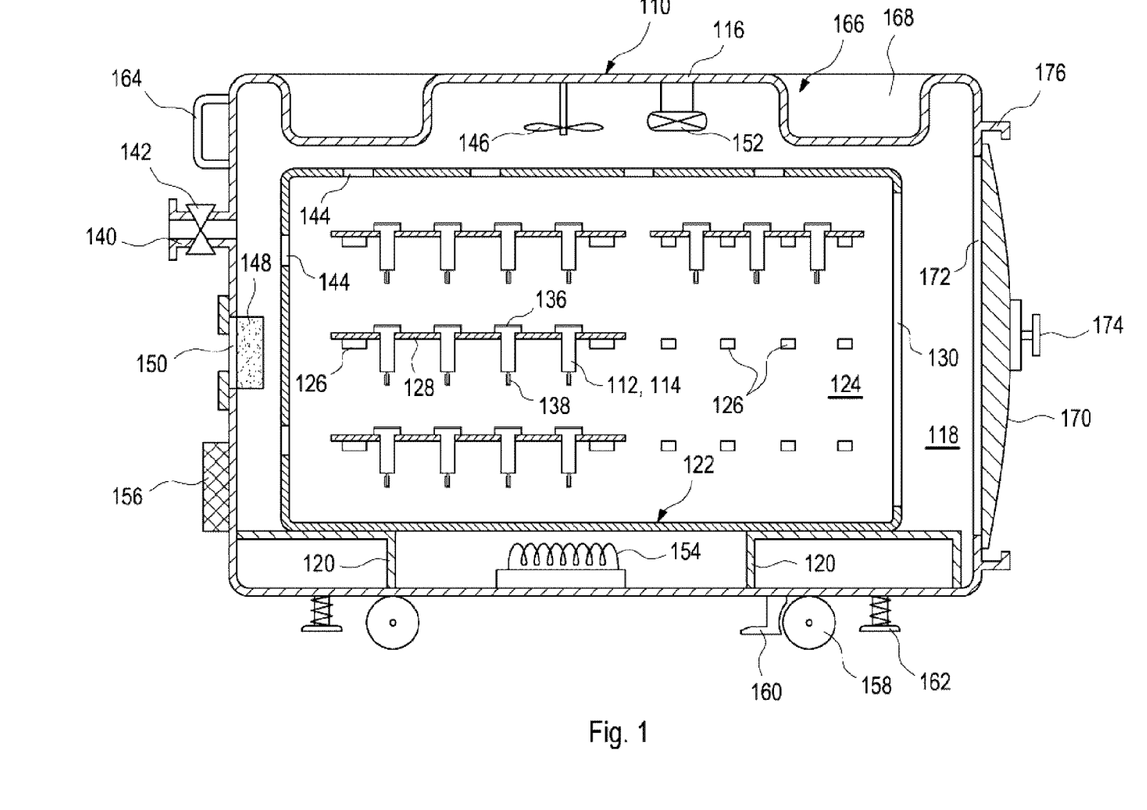
FIG. 1 is a schematic sectional illustration of a container according to the invention for the sterile transfer of syringe bodies.

FIG. 1 is a highly schematized sectional illustration from the side of an exemplary embodiment of a reusable container 110 according to the invention for the sterile transfer of pharmaceutical recipients 112. The pharmaceutical recipients 112 are configured in this exemplary embodiment as syringe bodies 114 without limiting the possibility of the use of further types of containers.

The container 110 has an outer case 116 which is configured in this exemplary embodiment as a one-walled outer case 116. Double or multiple-walled configurations, for example, are also possible. The outer case can for example be made of one or more of the above-mentioned materials and is intended in particular to ensure a dimensional stability in order to withstand the mechanical loads during transportation (for example stacking of a plurality of containers 110). Furthermore, the outer case 116 is to be able to withstand intensive cleaning and if appropriate disinfecting or sterilizing processes.

The outer case 116 encloses a sterilizable interior 118. Devices 120 for accommodating an inner container 122 are accommodated in this interior 118. These devices 120 can for example comprise rails, dovetail guides, fixing devices, threads, docking stations or the like.

The inner container 122 is in this simple exemplary embodiment according to FIG. 1 illustrated merely in highly schematized form. The inner container 122 is configured in this exemplary embodiment as a simple, cuboid container and is for example likewise made of the materials of relevance to the container 110. The inner container 122 should also ensure dimensional stability, even during loading with pharmaceutical recipients 112. For example, the inner container 122 can again be made of high-grade steel.

The inner container 122 is thus accommodated in the interior 118 of the container 110. The inner container 122 has for its part an interior 124 in which holders 126 for accommodating nests 128 are arranged. These holders 126 can in turn comprise various types of holders, for example rails for inserting the nests 128 through an opening 130 for loading the inner container 122.

Figure 2A:
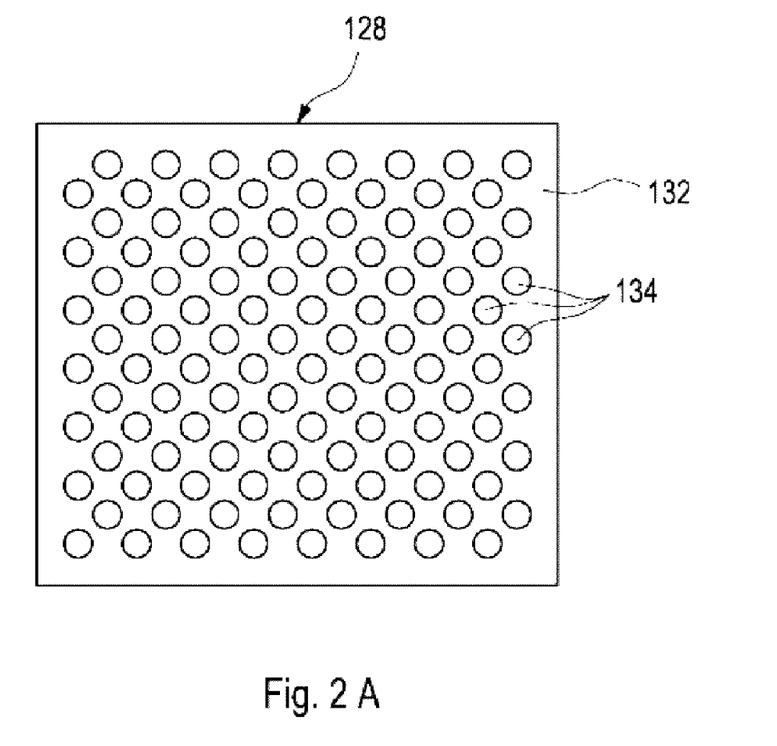
FIGS. 2A and 2B show two exemplary embodiments of various nests for accommodating syringe bodies.
Figure 2B:
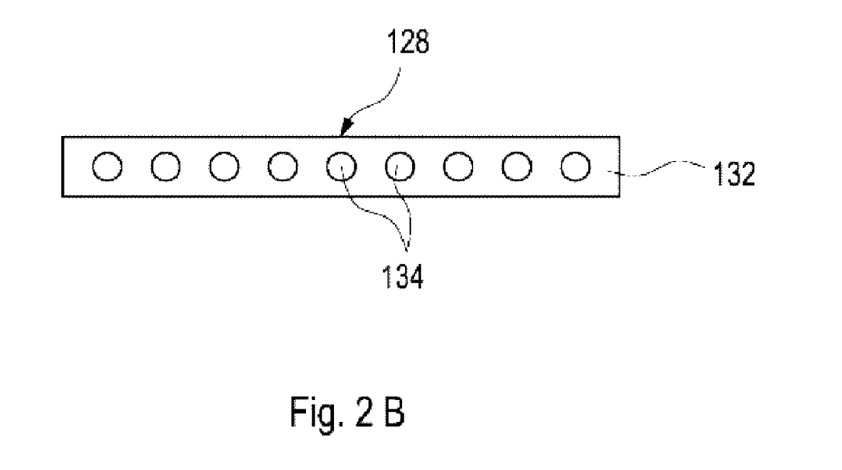

The nests 128 serve to accommodate the syringe bodies 114. FIGS. 2A and 2B are plan views of exemplary embodiments of nests 128 of this type. The nests 128 each have a nest body 132 of flat configuration. The nest body 132 can be configured as a reusable nest body and can accordingly comprise a dimensionally stable material which is resistant even to multiple cleaning and disinfecting processes, for example a plastics material (for example a fluorinated plastics material) and/or a metal, a ceramic or the like. Each nest body 132 has a large number of openings 134 for accommodating the syringe bodies 114. These openings 134 are configured in the illustrated exemplary embodiments as round bores in the nest body 132. In this case, FIG. 2A illustrates an exemplary embodiment of a nest 128 in which one hundred and twelve openings 134 are arranged in a substantially rectangular matrix with a hexagonal distribution. Every other row is in this case displaced from the preceding row by half the distance of an opening. In this way, it is possible to ensure optimum utilization of the space of the nest 128.

FIG. 2B, on the other hand, shows a nest 128 in which the openings 134 are arranged in a row.

The exemplary embodiments shown in FIGS. 2A and 2B are just two of a large number of possible exemplary embodiments of nests 128. Each container 110 or each inner container 122 preferably accommodates a large number of nests 128 of this type, so that for example each container 110 can be filled with several hundred to over 1,000 syringe bodies 114. The shape of the nests 128 can in particular also be adapted to the bottling plant to be loaded, wherein for example the arrangement in rows according to FIG. 2B may be suitable for serial plants (preferably what are known as line fillers) and the arrangement according to FIG. 2A may be suitable for plants with two-dimensional positioning of the syringe bodies 114 to be filled. In this case, the plants can for example be configured in such a way that the syringe bodies 114 are removed from the nests 128 before filling or, alternatively or additionally, filling can also take place in the nests 128.

As a result of the configuration of the nests 128, spatially and temporally ordered handling of the syringe bodies 114 is ensured in such a way that the removal of nests 128 and/or syringe bodies 114 from nests 128 under sterile conditions can be reversed during the pharmaceutical bottling process. In this case, syringe bodies 114 which have already been filled can be returned to the nests 128, again in ordered form, wherein the nests 128 can be located outside or within the container 110 and/or inner container 122. After this return of syringe bodies 114 which are still empty and/or syringe bodies 114 which have already been at least partly filled, the container 110 can be closed again and selectively even temporarily uncoupled from the sterile lock 184 and later recoupled, after which the emptying of the container 110 can be continued, as described hereinbefore, while maintaining the sterile conditions.

Furthermore, the shape of the openings 130 can also be adapted to the type of the pharmaceutical recipients 112 or to the particular features of the bottling plant, so that it is possible to provide, instead of continuous bores, for example also grooves in the edge of the nest body 132 according to FIG. 2B, into which the syringe bodies 114 can be laterally suspended. This might facilitate removal. A large number of possible configurations are conceivable. In particular, the holders 126 can also be adapted to the particular shape of the nest bodies 132.

As is shown partly and schematically in FIG. 1, the syringe bodies 114 and pharmaceutical recipients 112 respectively, which are inserted into the openings 134, can be closed at their upper end with an additional protective foil 136. However, this is not compulsory. Furthermore, the syringe bodies 114 can be closed at their lower end with a cap 138; this is likewise indicated symbolically in FIG. 1.

The pharmaceutical recipients 112 and the syringe bodies 114 respectively can for example be cleaned and disinfected or sterilized directly at the manufacturer's factory or in a further operation or part of operation after manufacture. Alternatively or additionally, the disinfection or sterilization can also take place wholly or partly in the interior 118 of the container 110 or a sterilized or disinfected state can be maintained in the interior 118 of the container 110. For this purpose, the container 110 has various means which can promote or effect disinfection or sterilization of this type. These means, all of which are optional and can be combined in any desired manner, can comprise various embodiments.

Thus, the container 110 illustrated in FIG. 1 has for example a port 140 on its rear wall. This port 140, which in this exemplary embodiment is for example provided with a valve 142 for closing the port 140, can in particular serve to introduce and/or discharge at least one fluid disinfecting medium and/or sterilizing medium into the interior 118. An additional opening can be provided, so that this sterilizing medium can be passed through the interior 118. The inner container 122 can also be provided with a corresponding port and/or an opening which allows the sterilizing medium (for example ethylene oxide) to be introduced. However, in the exemplary embodiment shown in FIG. 1, the inner container 122 has a simpler configuration with a plurality of openings 144 on its rear wall and its upper side. These openings 144 allow a fluid sterilizing medium to flow through the inner container 122.

Furthermore, in this exemplary embodiment, the container 110 has a ventilation device 146. This ventilation device 146 can ensure, for example during transportation and/or during a sterilization process, blending of the interior atmosphere in the interior 118 of the container 110 or in the interior 124 of the inner container 122. In the exemplary embodiment illustrated in FIG. 1, the ventilation device 146 is provided merely on the outer case 116. However, alternatively or additionally, further ventilation devices 146 can be provided, for example in the inner container 122.

Furthermore, in the exemplary embodiment illustrated in FIG. 1, the container 110 optionally has a microbial filter 148. In the exemplary embodiment illustrated in FIG. 1, the filter 148 is connected to an opening 150 in the container 110. This opening 150 can for example be configured as a closable opening. The microbial filter 148 ensures a germ-free atmosphere inside the container 110. Alternatively or additionally to the arrangement shown in FIG. 1 of the optional filter 148, a filter 148 can for example also be arranged on the inner container 122. Furthermore, alternatively or additionally, a filter 148 can also be provided with a circulating device, for example the ventilation device 146, in the interior 118 of the container 110 and/or in the interior 124 of the inner container 122, so that only circulated air or atmosphere is filtered inside the container 110 and air from the environment of the container 110 cannot infiltrate inside the container 110.

In the exemplary embodiment shown in FIG. 1, the container 110 and/or the inner container 122 has a radiation source 152 as further optional devices for ensuring sterility within the container 110. This radiation source 152, which can for example comprise an electromagnetic and/or radioactive radiation source 152, is securely integrated in the container 110 in the exemplary embodiment shown in FIG. 1. However, alternatively or additionally, it is also possible to provide in the container 110 or in the inner container 122 openings allowing merely temporary introduction of a radiation source 152 of this type for a disinfecting or sterilizing process.

As a further optional measure for maintaining or ensuring sterility in the container 110, a temperature control device 154 is provided in the exemplary embodiment shown in FIG. 1. In the exemplary embodiment shown, this temperature control device 154 is provided on the outer case 116; however, alternatively or additionally, it can also be provided in the interior 124 of the inner container 122. The temperature control device 154 is illustrated here as a simple heating coil, although other types of temperature control devices can also be provided. The temperature control device can preferably increase the temperature of the atmosphere in the interiors 118 and/or 124 of the container 110 or of the inner container 122 in order to ensure that there are no germs. However, alternatively or additionally, cooling devices are also conceivable, for example in order to prevent the spread and/or proliferation of microbial impurities. In this case, the interiors 118 and 124 respectively can for example be filled with a moisture-free inert gas, for example nitrogen or argon, in order to avoid condensations.

In the exemplary embodiment illustrated in FIG. 1, the container 110 further optionally has a controller 156. This controller 156 can for example contain its own power supply for the aforementioned devices for maintaining sterility in the container 110, for example a battery and/or an accumulator. Alternatively or additionally, it is also possible to provide terminals for an external power supply that can for example be connected to a corresponding power supply in a transport means and/or at the factory of the manufacturer of the pharmaceutical recipients 112, 114. Alternatively or additionally, the controller 156 can also contain control elements for actuating the aforementioned devices for maintaining or ensuring sterility in the container 110, for example switches, microprocessors, interfaces for connecting an external controller, input and output means (for example a display, keys, selection elements, etc.). The configuration of the controller 156 can in particular be adapted to the particular configuration of the means of the container 110.

The container 110 further has a plurality of means allowing simple transportation of the container 110. Thus, rolls or rollers 158, which can be equipped with a fixing and braking device 160, are in particular provided in the exemplary embodiment shown in FIG. 1. Furthermore, in addition to the rollers 158, there are optionally provided bearing feet 162 which can be extended during stationary storage of the container 110 (for example by way of a thread, an extendable device or the like) in order to ensure that the load on the rollers 158 is relieved and the container 110 is fixed. In order to simplify transportation, the container 110 can further comprise transport lugs 164 which are configured as simple grips in the exemplary embodiment 164 illustrated in FIG. 1. However, alternatively or additionally, it is also possible to provide a large number of further couplings for coupling a transport means, for example couplings for coupling transport hooks, etc.

Furthermore, in the exemplary embodiment illustrated in FIG. 1, the container 110 is equipped with outer shaped profiles 166 allowing a plurality of containers 110 to be stacked. In the exemplary embodiment illustrated in FIG. 1, these outer shaped profiles 166 have on the cover of the container 110 in particular depressions 168 in which the rollers 158, the fixing and braking devices 160 and the bearing feet 162 of a container 110 stacked thereover (not shown in FIG. 1) can be accommodated. In this way, the steadiness of stacked containers 110 can be increased and the containers 110 can be packed more tightly.

In order to microbially isolate the interiors 118 and 124 respectively of the container 110 from the environment of the container 110, the container 110 additionally has a container door 170 which closes a container opening 172. In the exemplary embodiment shown in FIG. 1, this container opening 172 is arranged on an end face of the container 110 and is designed in such a way that the inner container 122 can be inserted into the interior 118 of the container 110 through this container opening 172. As an alternative to the exemplary embodiment shown in FIG. 1, the container 110 can also accommodate a plurality of inner containers 122, wherein preferably a plurality of devices 120 for accommodating inner containers 122 of this type can be provided in this exemplary embodiment.

The container door 170 is illustrated in highly schematized form in FIG. 1 and has a closure mechanism 174, for example simple rotary closures, hooks, etc. In particular, the container door 170 used may, for example, be a bulkhead.

In the exemplary embodiment illustrated in FIG. 1, the container door 170 and the container opening 172 respectively are surrounded by a lock 176 for coupling the container to a sterile space. This lock 176 is configured in such a way that, when coupled, the container door 170 can be opened without atmosphere from the region surrounding the container 110 being able to infiltrate the interiors 118 and 124 respectively. Merely atmosphere from inside the sterile space or the lock of the sterile space (not shown in FIG. 1) can infiltrate the container 110 when the container door 170 is opened.

Various possibilities are conceivable for the configuration of the lock 176 of the container 110, the possibility of a bayonet closure being shown in highly schematized form in FIG. 1. For coupling, the lock 176 can also comprise movable, for example rotatable and/or pivotable and/or flexible (for example tubular) parts.

Figure 3:
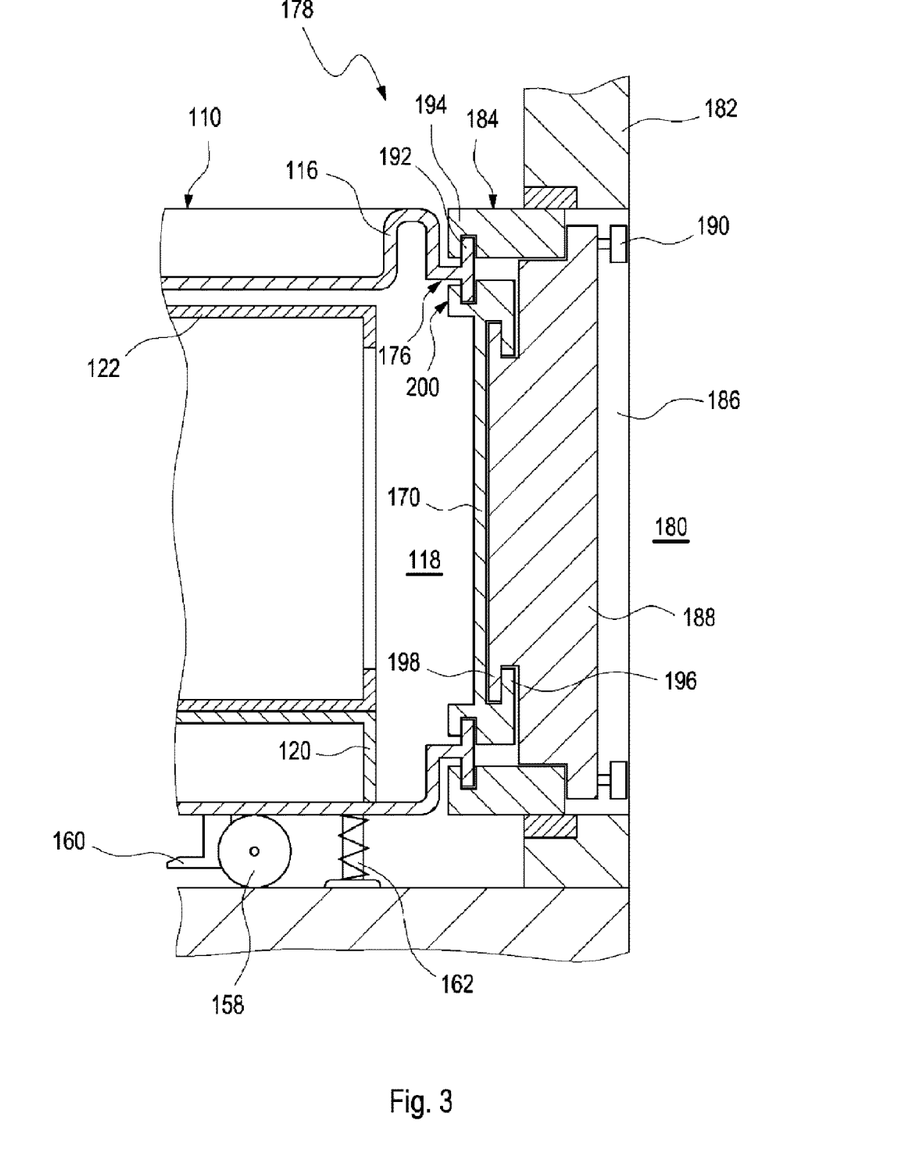
FIG. 3 is a sectional illustration of a detail of a transfer system according to the invention with a container coupled to a sterile lock.

FIG. 3 is a highly schematized sectional illustration of a possible configuration of a lock 176. FIG. 3 shows schematically a transfer system 178 comprising a container 110, for example according to the exemplary embodiment in FIG. 1, and an accessible sterile space 180. In the situation shown in FIG. 3, the container 110 is in this case connected via its lock 176 to a sterile lock 184 coupled to a sterile space wall 182. This sterile lock 184 can surround a sterile space opening 186 which can in particular be adapted to the dimensions of the container door 170. In this way, when the container 110 is coupled, the container door 170 can for example be opened out of the sterile space 180 without suspending the sterile internal atmosphere in the interior 118 of the container 110.

The sterile lock 184 comprises a sterile space door 188. In the non-coupled state, this sterile space door 188 closes the sterile space opening 186 by means of an interlocking mechanism 190 which is illustrated in FIG. 3 merely in highly schematized form. In the lock principle illustrated in FIG. 3, the lock 176 of the container 110 comprises a first lock part 192 which is connected to the outer case 116 of the container 110 outside the container door 170 and surrounds the container door 170, for example annularly. This first lock part 192 is for example configured as a peripheral projection, if appropriate provided with breaks, and allows coupling to a first sterile lock part 194. This first sterile lock part 194 surrounds substantially the sterile space opening 186 annularly and ensures, when coupled, a microbial isolation of the sterile space 180 and the interior 118 of the container 110. The first lock part 192 and the first sterile lock part 194 can for example interact in the form of a bayonet closure, wherein for example one of these two first lock parts 192, 194 or both of these parts can be configured rotatably in order to allow coupling and uncoupling.

If the first lock part 192 and the first sterile lock part 194 are joined together, then an intermediate space, which is generally non-sterile, can form between the container door 170 and the sterile space door 188. In order to ensure a minimum level of sterility here too, the lock 176 and/or the sterile lock 184 can for example be configured in such a way that this intermediate space is equipped with minimum volume. Alternatively or additionally, sterilizing means can also be provided in order to sterilize this intermediate space, for example before the container door 170 and/or the sterile space door 188 are opened. For this purpose, it is for example possible to provide, again, ports for introducing sterilizing media, heating means, radiation sources or the like, wherein reference may be made to the foregoing description concerning FIG. 1. Alternatively or additionally, a vacuum port can also be provided, so that this intermediate space can be briefly evacuated in order to be subsequently filled for example with sterile air from the sterile space 180 and/or with a sterile inert gas. In a similar manner, the port 140 in the container 110 can for example also be used to evacuate the interior 118 of the container 110 or the interior 124 of the inner container 122 and/or to fill it with a sterile inert gas and/or sterile atmosphere.

Alternatively or additionally to the aforementioned possibility of sterilizing the intermediate space between the container door 170 and sterile space door 188 during coupling of the container 110, FIG. 3 illustrates an embodiment in which the intermediate space between the container door 170 and the sterile space door 188 is almost completely avoided in that these two doors 170, 188 couple directly to each other. This direct coupling can in particular also allow the doors 170, 188 not to have to be opened separately and for example successively, but to be able to be opened simultaneously. For this purpose, the lock 176 can in particular comprise, in addition to the first lock part 192, a second lock part 196 which is arranged on the outer side of the container door 170. This second lock part 196 can for example again be configured in the form of a peripheral projection on the outer side of the container door 170, for example again as a part of a bayonet closure.

Similarly, the sterile lock 184 comprises a second sterile lock part 198 on the outer side of the sterile space door 188. This second sterile lock part 198, which can for example engage behind the projection of the second lock part 196, thus couples with the second lock part 196. For example, this coupling can, as described above, again comprise a bayonet closure.

In this case, the coupling mechanism can be configured in such a way that when the first lock part 192 is coupled to the first sterile lock part 194 (for example as a result of a rotary movement), the second lock part 196 is at the same time coupled to the second sterile lock part 198. As a result, on the one hand, the intermediate space between the two doors 170, 188 is preferably reduced to a minimum and the two doors 170, 188 are connected in a mechanically secure, for example rotationally fixed, manner. This allows the sterile space door 188 and the container door 170 to be simultaneously opened and/or closed, for example out of the sterile space 180. For this purpose, the container door 170 can for example comprise a bayonet closure 200 which can for example be opened or closed by rotating the sterile space door 188 which is coupled to the container door 170. Accordingly, the coupling between the second lock part 196 and the second sterile lock part 198 have to satisfy merely mechanical requirements, but not particular requirements in terms of sterility, as this coupling has to provide not microbial shielding, but merely mechanical coupling.

Presterilized pharmaceutical recipients 112 can thus be delivered to a bottling factory by means of the transfer system 178 shown in FIG. 3. The pharmaceutical recipients 112 can then be removed, when the sterile space 180 is coupled, from the container 110, directly or together with the nests 128. Complete removal of an optional inner container 122 is also possible and preferred. The pharmaceutical recipients 112 can then be filled in the sterile space 180. The inner containers 122 which are no longer required and/or the nests 128 which are no longer required can then be returned to the container 110, the doors 170, 188 can be closed and the lock 176 can be uncoupled. Subsequently, the container 110 can for example be returned to a manufacturer of the pharmaceutical recipients 112 in order to be reused there and for example to be refilled with pharmaceutical recipients 112. The illustrated transfer system 178 thus allows the process of filling syringe bodies to be streamlined and sped up considerably, as semi-automatic or automatic unloading is for example also possible in addition to removing the pharmaceutical recipients 112 from the container 110 by hand. Furthermore, much less waste is produced and it is possible to significantly reduce the costs of removing additional seals (for example welds).

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

| List of reference numerals | |
|---|---|
| 110 | container |
| 112 | pharmaceutical recipients |
| 114 | syringe bodies |
| 116 | outer case |
| 118 | interior of the container |
| 120 | devices for accommodating the inner container |
| 122 | inner container |
| 124 | interior of the inner container |
| 126 | holders for accommodating the nests |
| 128 | nests |
| 130 | opening for loading the inner container |
| 132 | nest body |
| 134 | openings for accommodating the syringe bodies |
| 136 | protective foil |
| 138 | cap |
| 140 | port |
| 142 | valve |
| 144 | openings for sterilization |
| 146 | ventilation device |
| 148 | filter |
| 150 | opening in the container |
| 152 | radiation source |
| 154 | temperature control device |
| 156 | controller |
| 158 | rolls |
| 160 | fixing and braking device |
| 162 | bearing feet |
| 164 | transport lugs |
| 166 | outer shaped profiles |
| 168 | depressions |
| 170 | container door |
| 172 | container opening |
| 174 | closure mechanism |
| 176 | lock |
| 178 | transfer system |
| 180 | sterile space |
| 182 | sterile space wall |
| 184 | sterile lock |
| 186 | sterile space opening |
| 188 | sterile space door |
| 190 | interlocking mechanism |
| 192 | first lock part |
| 194 | first sterile lock part |
| 196 | second lock part |

-continued

| List of reference numerals | |
|---|---|
| 198 | second sterile lock part |
| 200 | bayonet closure of the container door |

What is claimed is:

1. A reusable container for the sterile transfer of pharmaceutical recipients, comprising:
    an outer case defining a sterilizable interior, the interior being microbially isolated from the environment of the container;
    a holder disposed in the interior and configured for removably accommodating a nest for storing a plurality of pharmaceutical recipients;
    a container door for removing or introducing the nest into the interior; and
    a lock for coupling the container to a sterile space, the lock being configured such that, after coupling to the sterile space, the container door can be opened without substantially suspending sterility;
    wherein the lock comprises a first lock part connected to the outer case outside the container door and a second lock part connected to the container door, wherein the first lock part is coupleable to a first sterile lock part surrounding a sterile space door and wherein the second lock part is coupleable to a second sterile lock part connected to the sterile space door.

2. The container of claim 1, wherein the first lock part at least partly surrounds the container door.

3. The container of claim 1, wherein the lock has at least one bayonet closure.

4. The container of claim 1, wherein the container door comprises a pivoting door arranged on the container.

5. The container of claim 1, further comprising an inner container which can be accommodated in the interior, wherein the holder for accommodating the nest is accommodated at least partly in the inner container, the inner container and the container door being configured such that the inner container is reversibly removable from the interior.

6. The container of claim 5, wherein the inner container comprises an open inner container through which fluid sterilizing media can flow.

7. The container of claim 1, wherein the holder comprises at least one rail for inserting the nest.

8. The container of claim 1, further comprising a plurality of nests for storing a plurality of pharmaceutical recipients.

9. The container of claim 8, wherein the nests comprise at least one substantially planar nest body, the substantially planar nest body having a plurality of openings for accommodating the pharmaceutical recipients.

10. The container of claim 8, wherein the nests are disposed in the container without an individual, closed casing.

11. The container of claim 1, further comprising a port for introducing and/or discharging at least one fluid disinfecting medium and/or sterilizing medium into or from the interior.

12. The container of claim 1, further comprising at least one ventilation device for at least partly blending an atmosphere in the interior.

13. The container of claim 1, further comprising at least one opening for introducing a radiation source into the interior.

14. The container of claim 1, further comprising at least one radiation source for emitting radioactive radiation and/or electromagnetic radiation for disinfecting and/or sterilizing the interior.

15. The container of claim 1, further comprising at least one temperature control device for heating and/or cooling the interior.

16. The container of claim 1, further comprising at least one microbial filter for filtering atmosphere circulated in the interior and/or for filtering fluid media infiltrating the interior.

17. The container of claim 1, further comprising a plurality of rollers having brakes for transporting the container.

18. The container of claim 1, further comprising a plurality of bearing feet for mounting the container to a surface.

19. The container of claim 1, wherein the container comprises outer shaped profiles configured such that a plurality of containers can be stacked.

20. The container of claim 1, further comprising at least one externally accessible coupling for coupling a transport means.

21. The container of claim 1, wherein the container is configured as substantially dimensionally stable and is formed from at least one of the following materials: a metal, a ceramic, a glass, a plastics material and a composite material.

22. A transfer system for the sterile transfer of pharmaceutical recipients to a sterile space, comprising:
    at least one container as claimed in claim 1; and
    at least one sterile space accessible by the at least one container;
    wherein, the sterile space comprises a sterile space wall having a sterile lock, the sterile lock being coupleable to the lock of the container.

23. The transfer system of claim 22, wherein the sterile space comprises at least one bottling line for bottling at least one pharmaceutical medium into pharmaceutical recipients.

24. A method for filling pharmaceutical recipients with at least one pharmaceutical medium, the method comprising:
    providing a plurality of sterilized pharmaceutical recipients;
    arranging the sterilized pharmaceutical recipients in at least one nest;
    introducing the nest into the interior of a reusable container comprising an outer case with a sterilizable interior and a door for removing or introducing the nest into the interior;
    using a lock of the container to couple the container to a sterile space;
    opening the container without substantially suspending sterility;
    transferring the nest and/or the pharmaceutical recipients to the sterile space through the container door; and
    introducing the at least one pharmaceutical medium into the pharmaceutical recipients.

25. The method of claim 24, wherein the pharmaceutical medium is introduced by a line filler installation or a tray filler installation.

26. The method of claim 24, further comprising subsequently uncoupling the reusable container from the sterile space and transporting the reusable container.

27. The method of claim 24, further comprising returning at least one nest or inner container that is partially filled with pharmaceutical recipients to the container.

28. A transfer system for the sterile transfer of pharmaceutical recipients to a sterile space, comprising:
    a reusable container, comprising:
        an outer case defining a sterilizable interior, the interior being microbially isolated from the environment of the container;

a holder disposed in the interior and configured for removably accommodating a nest for storing a plurality of pharmaceutical recipients;
a container door for removing or introducing the nest into the interior;
a container lock; and
a sterile space accessible by the reusable container, comprising:
a sterile space door; and
a sterile space lock;
wherein, the container lock is coupleable to the sterile space lock, after which the container door can be opened without substantially suspending sterility.

29. The transfer system of claim 28, wherein:
the container lock comprises a first lock part connected to the outer case outside the container door and a second lock part connected to the container door;
the sterile space lock comprises a first sterile lock part surrounding a door of the sterile space and a second sterile lock part connected to the sterile space door; and
the first lock part is coupleable to the first sterile lock part and the second lock part is coupleable to the second sterile lock part.

30. The transfer system of claim 28, wherein the sterile space comprises at least one bottling line for bottling at least one pharmaceutical medium into pharmaceutical recipients.

31. The transfer system of claim 28, wherein the reusable container comprises a plurality of nests for storing a plurality of pharmaceutical recipients.

32. The transfer system of claim 31, wherein the nests comprise at least one substantially planar nest body, the substantially planar nest body having a plurality of openings for accommodating the pharmaceutical recipients.

33. The transfer system of claim 31, wherein the nests are disposed in the reusable container without an individual, closed casing.

* * * * *